United States Patent [19]
Ward et al.

[11] Patent Number: 4,522,758
[45] Date of Patent: Jun. 11, 1985

[54] METHOD OF PREPARING 2-FLUORO-17β-ESTRADIOL

[75] Inventors: John S. Ward; C. David Jones, both of Indianapolis, Ind.

[73] Assignee: Eli Lilly and Company, Indianapolis, Ind.

[21] Appl. No.: 564,595

[22] Filed: Dec. 22, 1983

[51] Int. Cl.³ ................................................ C07J 1/00
[52] U.S. Cl. .................................................... 260/397.5
[58] Field of Search ....................................... 260/397.5

[56] References Cited

PUBLICATIONS

J.C.S. Chem. Comm. (1981) 217, p. 1157, article by Santaniello.
Liehr, *Molecular Pharmacology*, 23, 278 (1983).
Utne et al., *J. Org. Chem.* 33, 2469 (1968).
Neeman et al., *J. Chem. Soc.* (Perkin Trans. 1) 2300 (1972).
Palmer et al., *J. Labelled Compds.*, 16, 14 (1979).
Eakins et al., *Int. J. App. Rad. & Iso.*, 30, 695 (1979).
Heiman et al., *J. Med. Chem.*, 23, 994 (1980).
Goswami et al., *id*, 1002.
Ng et al., *J. Org. Chem.*, 46, 2520 (1981).
Santaniello, *J.C.S. Chem. Comm.*, 217, 1157 (1981).
Njar et al., *J. Org. Chem.*, 48, 1007 (1983).
Rozen et al., *J.C.S. Chem. Comm.*, 443 (1981).
Shiue, *J. Nucl. Med.*, 23, 899 (1982).
Mantescu et al., *Radiopharm. & Labelled Compds.*, 395 (1973).

*Primary Examiner*—Elbert L. Roberts
*Attorney, Agent, or Firm*—James L. Rowe; Arthur R. Whale

[57] ABSTRACT

2-Fluoro-17β-estradiol is synthesized by mercurating a 17β-estradiol diacylate or dietherate at C-2, replacing the mercury group with fluorine and then cleaving the acyl or ether protecting groups.

7 Claims, No Drawings

METHOD OF PREPARING 2-FLUORO-17β-ESTRADIOL

BACKGROUND OF THE INVENTION

Liehr, *Molecular Pharmacology*, 23, 278 (1983) discloses the fact that, as contrasted with 17β-estradiol, 2-fluoro-17β-estradiol did not induce renal clear-cell carcinoma in male Syrian hamsters at equipotent estrogenic doses.

Thus, there is a renewed interest in 2-fluoro-17β-estradiol which compound was first described by Utne et al. *J. Org. Chem.*, 33, 2469 (1968). The Utne procedure involved nitration of estrone in the 2-position and the 4-position, separation of the two isomers, conversion of the 3-phenolic hydroxyl of the 2-nitro estrone to an ether, reduction of the nitro group to an amine, diazotization of the amine including preparation of the fluoroborate salt, decomposition of the salt to yield 2-fluoroestrone 3-methyl ether, reduction of the 17-ketone group with sodium borohydride and demethylation of the ether to regenerate the phenol. This procedure involves many steps, the initial nitration produces a mixture of isomers, and the yields are not as high as would be desirable in a commercial process.

Neeman et al. *J. Chem. Soc.* (Perkin Transactions 1), 1972, 2300 used a different approach to the preparation of 2-fluoro-17β-estradiol. This approach involved employing, as a starting material, 10β-hydroxyestr-4-ene-3,17-dione. This compound was epoxidized to yield the 4β,-5β-epoxy derivative and the epoxy compound fluorinated with gaseous hydrogen fluoride in chloroform-ethanol to yield, ultimately, a 2-fluoro-10β-hydroxyestr-4-ene-3,17-dione. Dehydration of this compound with thionyl chloride produced 2-fluoroestrone, reduction of which with sodium borohydride yielded 2-fluoro-3,17β-estradiol.

The ultimate starting material for the Neeman synthesis, 19-nortestosterone, is not readily obtainable. The authors also refer to their prior specific synthesis of 4-fluoro-17β-estradiol, a compound also prepared by Palmer et al. *J. Labelled Cmpds.*, 16, 14–16 (1979) and by Eakins et al.—see *International Journal of Applied Radiation and Isotopes*, 30, 695 (1979). These latter authors also prepared 4-fluoroestrone, 2,4-diiodoestradiol and 2-iodoestradiol. 2-Iodo-17β-estradiol was prepared from 17β-estradiol and sodium iodide. The preparation involved evaporation of any solvent and melting the two solid materials together at 180° C. Since radioactive iodine had been used, autoradiography could be used to distinguish the desired 2-iodo-17β-estradiol from all other substances in the mixture; thus separation by chromatography was possible. These radioactively labelled compounds, $I^{125}$-2-iodoestradiol and $F^{18}$-4-fluoroestradiol, were designed for use in scanning for estrogen dependent tumors or for scanning the prostate.

Heiman et al., *J. Med. Chem.*, 23, 994 (1980) sought superior methods of preparing halogenated estrogens for use as estrogen receptor-based imaging agents. The authors prepared 3-fluorohexestrol by procedures similar to those employed by Utne et al. (loc. cit.) for preparing 2-fluoro-17β-estradiol.

An adjacent paper by the same group of authors, Goswami et al., *J. Med. Chem.*, 23, 1002 (1980), discusses the preparation of side-chain halogenated hexestrol derivatives.

A third paper from the same group, Ng et al., *J. Org. Chem.*, 46, 2520 (1981), describes the fluorination of hexestrol (a phenolic estrogen), ortho to the phenol group, during which process an amine group is converted to an arylazide and the azide decomposed in the presence of HF. In this last step, fluorine replaces the azide grouping.

Santaniello et al., *J.C.S. Chem. Comm.*, 1981, 217, 1157 (1981) attempted to prepare orthohalogen derivatives of estradiol or of the corresponding ethers or acyl compounds. The authors regioselectively chloromercurated the $C_2$-position of 3-methoxy-17β-acetoxyestra-1,3,5-triene. This chloromercury derivative was readily converted to a 2-bromo and a 2-iodo derivative with $Br_2$ or $I_2$ respectively. An expansion of the original paper can be found in *J.C.S. Chem. Comm.*, 1157, (1982).

Njar et al., *J. Org. Chem.*, 48, 1007 (1983) describe the synthesis of 4-fluoro-17β-estradiol, 4-fluoroestrone and similar compounds. 4-Fluoro-17β-estradiol was prepared from 4-fluoro-19-nortestosterone by dehydrogenation with selenium dioxide.

Adam et al., *Can. J. Chem.*, 61, 658 (1983) describe the preparation of fluorobenzene from phenyl mercury trifluoroacetate and elemental fluorine.

The reagent, acetyl hypofluorite, has been described by Rozen et al., *J.C.S. Chem. Comm.*, 443 (1981) who describe this compound as a new electrophilic fluorinating agent.

Shiue et al., *J. Nucl. Med.*, 23, 899 (1982) used $^{18}F$-labeled acetyl hypofluorite to fluorinate 2-deoxy-D-glucose. Yields were about 20%.

Mantescu et al., *Radiopharm. and Label Cmpds.*, 395 (1973) employed a mixture of glacial acetic acid and $K^{18}F$ as a fluorinating agent to prepare certain steroid hormones containing radioactive fluorine. These hormones included 4-fluorotestosterone and 2,4-difluoroestrone. The authors adopted the procedure of iodinating estrone at the 2 and 4 carbons and then replacing the iodine with radiofluorine using the KF-acetic anhydride procedure.

It is apparent that no commercially feasible synthetic route is available for preparing 2-fluoro-17β-estradiol; i.e., a route based on readily available and inexpensive starting materials, employing a minimal number of steps and capable of giving good yields of all products. It is an object of the invention to provide such a procedure.

SUMMARY OF THE INVENTION

In fulfillment of the above and other objects, this invention provides a method for preparing 2-fluoro-17β-estradiol by mercurating an estradiol derivative of formula I having protected hydroxyl groups at C-3 and C-17 with a mercurating agent such as mercury trifluoroacetate in trifluoroacetic acid to yield a compound of structure II. Reaction of this intermediate with acetyl hypofluorite produces 2-fluoro-17β-estradiol protected at C-3 and C-17 according to structure III. Deprotection (removal of ester or ether protecting groups by standard procedures) yields 2-fluoro-17β-estradiol (IV).

The above reaction scheme is illustrated in the following flow chart. Mercury trifluoroacetate in trifluoroacetic acid is used as the mercurating agent for illustrative purposes only.

FLOW CHART

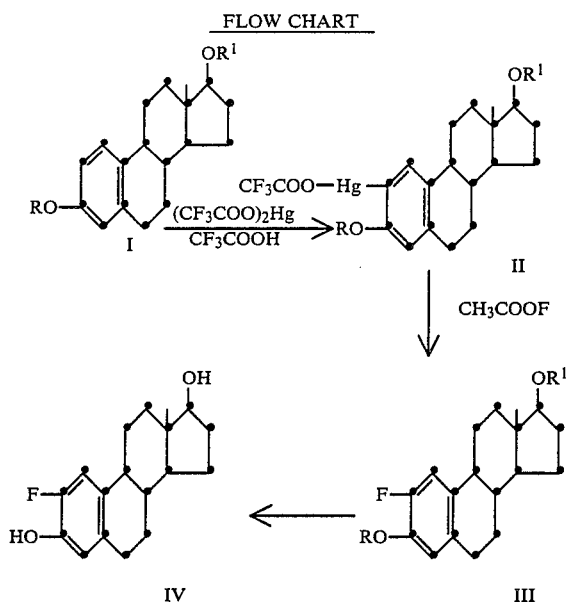

wherein R and R[1] are separately acid-stable hydroxy protecting groups. By the term "acid-stable" is meant an hydroxy protecting group which is stable in the presence of trifluoroacetic acid or the like acid used as a solvent in the above reaction scheme in the absence of compounds with an unprotected hydroxyl.

In the above procedure, the acid-stable hydroxy protecting group (stable to acidic solvents such as CF$_3$COOH under the reaction conditions or to acid containing reaction media) can be an ether such as a lower alkyl ether or can be an ester such as a formate, lower-alkanoate, fluoro-substituted-lower alkanoate, benzoate, lower alkyl sulfonate or aryl sulfonate. Acid-stable, lower-alkyl ether protecting groups include the methyl, ethyl, isopropyl and n-propyl ethers. Lower-alkanoyl or fluoro-substituted lower-alkanoyl protecting groups, also acid-stable, include the acetate, propionate, isobutyrate, n-butyrate, trifluoroacetate and the like groups. Finally, lower-alkylsulfonyl protecting groups include methane sulfonate (mesylate), trifluoromethane sulfonate, ethane sulfonate and the like, while aryl sulfonate protecting groups include benzene sulfonate, tosylate and the like.

In the above flow chart, the mercurating agent has been specified as mercuric trifluoroacetate and the solvent as trifluoroacetic acid or acetic acid. Other mercurating agents such as mercuric acetate, mercuric nitrate, mercuric fluoride and the like in trifluoroacetic acid or acetic acid can also be used. The extent and selectivity of the mercuration, C-2 versus C-4, depends in large part upon the nature of the protecting group. We have found that, with acetate protecting groups (R and R[1] are CH$_3$—CO in formulas I, II and III), mercuration is substantially exclusively at C-2; hence, the synthetic procedure yields a 2-mercurated derivative which can be transformed to 2-fluoro-17$\beta$-estradiol essentially free from any 4-fluoro products. With certain protecting groups, some C-4 mercuration may occur. Separation of the 4-mercurated 17$\beta$-estradiols from 2-mercurated 17$\beta$-estradiols as by chromatography can be used to provide, eventually, 2-fluoro-17$\beta$-estradiol free from products carrying a 4-fluoro group. Alternatively, any 4-fluoro compound can be removed at either the 17$\beta$-diprotected stage of the synthetic procedure (III) or as final products (IV). It is an advantage of using the 3,17$\beta$-diacetate as a starting material that production of isomeric products is minimal.

In addition to a proper choice of protecting groups, in order to prepare substantially pure 2-fluoro-17$\beta$-estradiol, the solvent and reagents should be free from other halogens which would be exchangeable with F under the reaction conditions. Presence of chloride, for example, in the reaction medium or as part of the mercury-containing group at C-2 might result in coproduction of 2-chloro-17$\beta$-estradiol.

In the acetyl hypofluorite reaction, trifluoroacetic acid has been specified as the mutual inert solvent, but it will be apparent to those skilled in the art that other equivalent acidic solvents could be employed. It should be emphasized, however, that the solvent, as well as the acetyl hypofluorite reagent itself should be substantially free of other exchangeable halogens to avoid the inadvertent production of other 2-halo-17$\beta$-estradiols.

Finally, the protecting groups, R and R[1], must be removed from the product III in order to obtain the useful final product, 2-fluoro-17$\beta$-estradiol (IV). If the protecting group is an ester group, base hydrolysis is usually employed, using an alkali metal hydroxide or carbonate as the base. Reduction with LiAlH$_4$ can also be used as can trans-esterification using an alcohol like methanol and a acidic catalyst. The methyl ether protecting groups can be cleaved with such reagents as pyridine hydrochloride or AlBr$_3$ in the presence of ethyl mercaptan or by other established ether cleavage methods. Ether cleavage procedures for phenolic ethers have almost universally been worked out for the methyl ether. Hence, the methyl ether is the preferred ether protecting group. However, those skilled in the art could readily adapt procedures for cleaving a methyl ether to cleavage of higher alkyl ethers. For more detailed information as to use and cleavage of hydroxy protecting groups, see Greene, *Protecting Groups in Organic Synthesis*, Chapters 2 and 3 (John Wiley & Sons, N.Y.-1981).

When R and R' are both acetyl in the above synthesis, up to 30% yields of 2-fluoro-17$\beta$-estradiol diacetate are obtained substantially free from contaminating 4-fluoro products. Hydrolysis of the two acetate groups is virtually quantitative (95%). Thus, the use of the diacetate of 17$\beta$-estradiol as a starting material constitutes a preferred species of our invention.

This invention is further illustrated by the following specific example.

EXAMPLE 1

Preparation of 3,17$\beta$-estradiol diacetate

Although 3,17$\beta$-estradiol diacetate is commercially available, as is 17$\beta$-estradiol, we prepared the diacetate from 3,17$\beta$-estradiol according to the following procedure.

A reaction mixture was prepared from 10.8 g. of 3,17$\beta$-estradiol, 40 ml. of acetic anhydride and 15 g. of polymeric polyvinyl pyridine in 200 ml. of anhydrous chloroform. The reaction mixture, a suspension, was heated to reflux temperature overnight. The volatile constitutents were removed at about 40° C. The resulting residue was dissolved in a mixture of from 1200–1500 ml. of ethyl acetate and 500 ml. of water. This new mixture was stirred for about 15–20 minutes at ambient temperature after which time the polymer was separated by filtration. The filtered polymer was rinsed with additional ethyl acetate. The ethyl acetate filtrate and wash were combined and the combined layer washed twice with water. The water layer was also extracted with ethyl acetate and this ethyl acetate extract added to the ethyl acetate filtrate. The combined ethyl acetate fractions were given a final water wash and were then dried. Evaporation of the ethyl acetate in vacuo yielded an oil which crystallized upon scratching. Yields of 3,17β-estradiol 3,17β-diacetate in two runs of the above quantities gave 13 and 13.1 g. of the desired product; yield=92–93%.

EXAMPLE 2

Preparation of 2-trifluoroacetylmercury-3,17β-estradiol diacetate

About 10 g. of 3,17β-estradiol 3,17β-diacetate were dissolved in 15 ml. of trifluoroacetic acid and the solution cooled to about 0° C. Twelve grams of mercuric trifluoroacetate were added and the reaction mixture stirred at ice bath temperatures for about 3.5 hours. The solvent was then removed by evaporation in vacuo and the residual material dissolved in methylene dichloride. The methylene dichloride solution was extracted with water and the water extract discarded. The methylene dichloride layer was dried with anhydrous sodium sulfate. The drying agent was removed by filtration and the methylene dichloride evaporated from the filtrate in vacuo. The resulting residual foam was triturated with hexane by sonication for about one hour to produce crystals. The crystallization mixture was filtered and the filter cake rinsed with hexane. About 17.2 g. of the 2-trifluoroacetyl mercury derivative were obtained (92% yield).

EXAMPLE 3

Preparation of 2-fluoro-3,17β-estradiol 3,17β-diacetate

The acetyl hypofluorite reagent was prepared as follows.

A suspension of 5 g. of sodium acetate in 50 ml. of glacial acetic acid was added to 550 ml. of Freon 11 with stirring. The mixture was cooled to about −80° C. in a dry ice-acetone bath while nitrogen was being bubbled through the reaction mixture. When the reaction mixture had attained the desired temperature, a stream of 18% fluorine in nitrogen was bubbled in. After five to six hours, a 2 ml. aliquot was added to 20 ml. of 60% aqueous acetic acid containing 1.5 g. of potassium iodide. The iodine generated was completely oxidized by 5.8 ml. of 0.1N sodium thiosulfate which indicated that the solution was approximately 0.145 molar in acetyl hypofluorite.

Two grams of 2-trifluoroacetylmercury-17β-estradiol diacetate were dissolved in 25 ml. of chloroform. To this stirred solution was added 25 ml. of the 0.145 molar acetyl hypofluorite mixture prepared as described above. After about 10 minutes, the mixture was combined with other similar reaction mixtures. The combined reaction mixtures were then washed with water, with aqueous saturated sodium bicarbonate and again with water. The extracts were then dried. Evaporation of the solvent in vacuo yielded a residual yellowish oil.

Thirty-eight similar runs employing a total of 76 g. of the 2-trifluoroacetylmercury-17β-estradiol diacetate starting material were combined and the combined residues obtained after workup, were chromatographed over silica gel using a 10% ethyl acetate—90% isooctane solvent mixture as the eluant. Those fractions containing 2-fluoro-17β-estradiol diacetate as determined by NMR analysis were combined to give 9.5 g. of the desired compound. This material was dissolved in toluene and rechromatographed over a Prep 500 silica gel column with toluene as the eluant. Seven and seven tenths grams of the desired 2-fluoro-17β-estradiol diacetate were thus obtained.

Three and six tenths grams of 2-fluoro-17β-estradiol diacetate were suspended in 48 ml. of methanol and 15 ml. of water. A solution of 2.4 g. of potassium hydroxide in 29 ml. of water was added. The reaction mixture was stirred overnight at ambient temperature. The volatile constituents were removed in vacuo and the resulting residue suspended in 1N aqueous hydrochloric acid. This suspension was slurried with ethyl acetate until two clean layers formed. The aqueous layer was separated and the separated layer washed with additional ethyl acetate. The ethyl acetate extracts were combined and the combined extracts washed twice with water and then dried. The combined solutions were concentrated to less than 50 ml. and crystallization induced by scratching. The crystallizing solution was placed at about 0° C. overnight. Crystals thus produced were separated by filtration and the filter cake washed with pre-cooled methanol. Two and nine hundredths grams of 2-fluoro-17β-estradiol were obtained in this way. The compound crystallized with ½ mole of methanol.

Analysis for the hemimethanolate of 2-fluoro-17β-estradiol was as follows:

Calculated: C, 72.51; H, 8.22 Found: C, 72.30; H, 8.49 Yield from diacetate=75%.

The above procedure is equally adaptable to the preparation of 2-fluoro-17β-estradiol.

In addition to providing 2-fluoro-17β-estradiol as an estrogenic substance, the above procedure provides 2-$^{18}$F-17β-estradiol useful in position emission tomography in estrogen dependent tumors, etc. As previously stated, 2-fluoro-17β-estradiol has a lower cancer-inducing potential than 17β-estradiol. In addition, 2-fluoro-17β-estradiol is metabolized more slowly than 17β-estradiol and thus lower dose levels may be used to provide equal estrogenic activity.

We claim:

1. The method of preparing 2-fluoro-17β-estradiol which comprises (1) mercurating at C-2 with a mercurating agent in a mutual inert solvent, said mercurating agent and solvent being free from other halogens exchangeable with fluorine under the reaction conditions, a steroid of the structure

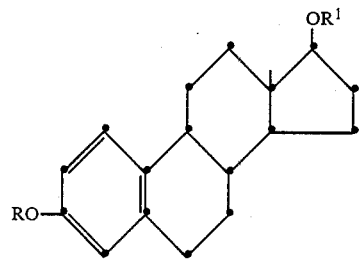

wherein R and R$^1$ are acid-stable hydroxyl protecting groups;

(2) reacting said 2-mercurated derivative with acetyl hypofluorite in a mutual inert solvent, thereby replacing said mercury containing group at C-2 with fluorine to yield a 2-fluoro-17β-estradiol having acid-stable hydroxy-protecting group at the 3 and 17β-hydroxyls; and (3) then removing said hydroxyl protecting groups.

2. A process according to claim 1 in which the hydroxyl protecting groups, R and R$^1$, are separately lower alkyl ethers or lower alkanoyl esters.

3. A process according to claim 2 in which the hydroxyl protecting groups, R and R$^1$, are lower acetyl groups.

4. A process according to claim 1 in which the mercurating agent is selected from (1) mercuric trifluoroacetate, (2) mercuric acetate in trifluoroacetic acid, and (3) mercuric fluoride in trifluoroacetic acid or acetic acid.

5. A process according to claim 4 in which the mercurating agent is mercuric trifluoroacetate.

6. A process according to claim 1 in which the mutual inert solvent for the mercuration step is trifluoroacetic acid.

7. A process for preparing 2-fluoro-17β-estradiol which comprises mercurating 3,17β-estradiol 3,17β-diacetate with mercuric trifluoroacetate at C-2 in trifluoroacetic acid as a solvent, contacting said 2-trifluoroacetyl mercurated derivative with acetyl hypofluorite to form 2-fluoro-3,17β-estradiol 3,17β-diacetate, and then removing the acetate groups to provide 2-fluoro-17β-estradiol.

* * * * *